United States Patent [19]

LeMaistre et al.

[11] Patent Number: 5,137,806
[45] Date of Patent: Aug. 11, 1992

[54] METHODS AND COMPOSITIONS FOR THE DETECTION OF SEQUENCES IN SELECTED DNA MOLECULES

[75] Inventors: Anne LeMaistre, Humble; Ming-Shen Lee, Houston, both of Tex.

[73] Assignee: Board of Regents, The University of Texas System, Austin, Tex.

[21] Appl. No.: 448,118

[22] Filed: Dec. 11, 1989

[51] Int. Cl.[5] .................... C12Q 1/68; C12Q 1/00; C12P 19/34; C07H 15/12
[52] U.S. Cl. ............................ 435/6; 435/91; 435/810; 536/27; 536/28; 935/6; 935/17; 935/19; 935/27; 935/77; 935/78; 436/501
[58] Field of Search ............... 435/6, 91, 805, 948, 435/810, 803, 7; 436/27, 501, 811; 935/6, 17, 19, 78, 88

[56] References Cited

U.S. PATENT DOCUMENTS

| 4,656,127 | 4/1987 | Mundy | 435/6 |
| 4,683,195 | 7/1987 | Mullis et al. | 435/6 |
| 4,851,331 | 7/1989 | Vary | 435/6 |
| 4,883,750 | 11/1989 | Whiteley et al. | 435/6 |

FOREIGN PATENT DOCUMENTS 333465 9/1989 European Pat. Off. .

OTHER PUBLICATIONS

Newton and Markham, European Patent Application, 0,332,435 (1989).
Newton et al. Nucl. Acid Res. 17(7): 2503–16 (1989).
Petruska et al. P.N.A.S. 85: 6252–56 (1988).
Ehlen et al. Bioch. Biophy. Res. Com. 160(2) 441–47 (1989).
Chien et al J. of Bact. 127(3):1550–57 (1976).
Wu et al. P.N.A.S. 86:2757–60 (1989).
Tindall et al. Biochem. 27(16): 6008–13 (1988).
Nasgal et al. Nucl. Acid Res. 18(10):3077–8 (1990).
Mullis et al. (1986) Specific. Enzymatic. amplification of DNA in Vitro: The Polymerase Chain Reaction. Cold Spr. Sym. V11.

*Primary Examiner*—Robert A. Wax
*Assistant Examiner*—Miguel Escallon
*Attorney, Agent, or Firm*—Arnold, White & Durkee

[57] ABSTRACT

The present disclosure relates to novel procedures and primers for use in conenction with PCR or in vitro DNA sequence amplification to detect sequence variants, such as sequence modifications or mutations. The invention will have particular applicability in the detection of point or other relatively short mutations where the expected location or configuration of the mutation is known. Primers of the invention incorporate a 3' terminal nucleotide or nucleotides complementary to the sequence variance, and thereby serve to successfuly prime chain elongation only on DNA templates which include the particular variant. Exemplary mutations suitable for detection through practice of the invention include those involved in beta-thalassemia, sickle cell anemia, hemoglobin C disease, diabetes, acute intermittent porphyria, lung, breast, and colon cancers and others.

22 Claims, 3 Drawing Sheets

METHODS AND COMPOSITIONS FOR THE DETECTION OF SEQUENCES IN SELECTED DNA MOLECULES

BACKGROUND OF THE INVENTION

1. Field of the Invention

The present invention relates to methods and compositions for detecting the presence or absence of a target DNA sequence, such as a mutation, within an identified region of a selected DNA molecule, such as a gene. In particular aspects, the invention relates to the use of novel primer constructs in connection with the polymerase chain reaction (PCR) technique for the detection of genetic mutations in genes, particularly point mutations.

2. Description of the Related Art

The ability to detect specific nucleotide alterations or mutations in DNA sequences such as genes is an invaluable tool for medical science. The ability to identify such alterations provides a means for diagnosis of genetic diseases that involve DNA mutations, including sickle-cell anemia, thalassemia, diabetes, certain oncogenic mutations, and the like. Importantly, the ability to diagnose genetic diseases such as the foregoing would provide numerous advantages, ranging from the ability to prepare for proper care and treatment of affected individuals, such as in the case of prenatal diagnosis, to marital counseling of prospective parents. Unfortunately, the techniques presently available to medical science for such diagnosis have been generally quite limited in one or more aspects.

One technique which has been used with some frequency employs the use of the PCR or site-specific DNA amplification technique, in combination with synthetic oligodeoxynucleotides. This technique, exemplified by the procedure set forth in Verlaan-de-Vries, et al.: A dot blot screening procedure for mutated ras oncogenes using synthetic oligonucleotides (Gene 50:313–320, 1986), involves the specific in vitro amplification of genetic regions suspected of containing a particular, known mutation in a specific configuration, followed by hybridization of the amplified DNA under tightly controlled parameters with one or more oligonucleotides which carry complementary mutations. By determining which of the oligonucleotides bind tightly under the specified hybridization conditions, one can attempt to ascertain which, if any, of the mutations are present in the segment of the DNA that is amplified. While this technique has shown some usefulness, it is quite cumbersome in that it requires several steps, including both an amplification step followed by a separate hybridization step. Furthermore, the technique relies upon very tightly controlled hybridization conditions, thus rendering it generally inapplicable to everyday clinical application.

A second approach which has found some usefulness in connection with certain genetic disorders involves the use of restriction enzyme analysis of DNA to identify changes in restriction fragmentation pattern of the suspected or selected DNA in comparison with a standard or reference DNA. In one approach employing restriction enzyme analysis, the selected and reference DNAs are simply compared, side-by-side, using various restriction enzyme digestions. An alteration in the digestion pattern of the selected DNA versus the reference DNA is indicative of a mutation, such as an insertion or deletion.

However, to identify very small mutations, such as point mutations or insertions or deletions of very short regions, the foregoing restriction enzyme analysis approach is often inapplicable. This is because it is very difficult to identify very small shifts in molecular weight of DNA fragments. In fact, in the case of very small mutations, restriction enzyme analysis is typically only applicable where the mutation involves the restriction enzyme target site itself. While some examples are known where direct restriction analysis is useful for identifying mutations, the foregoing technique is generally not applicable to a broad range of embodiments and is therefore quite limited in its usefulness. For example, while in the case of sickle-cell anemia the precise mutation is generally known (Saiki, et al.: Enzymatic amplification of beta-globin genomic sequences and restriction site analysis for diagnosis of sickle cell anemia. Science 230(1732):1350–4, 1985), in B-thalassemia, over 40 different possible mutations are known, generally ranging from about 1 to 3 basepairs. Therefore, this technique is not applicable where the genetic disease fails to create either a changed or new restriction site or where restriction fragment length polymorphism is not present.

An example of the foregoing direct restriction endonuclease analysis approach is disclosed in U.S. Pat. No. 4,395,486 to Wilson et al. The Wilson et al. patent teaches a method for the diagnosis of sickle cell anemia by a restriction endonuclease assay through the use of an enzyme, such as Dde I, which recognizes nucleotide base sequence CTNAG. The Wilson et al. method relies upon the discovery that the sickle cell trait involves a point mutation of the DNA at codon 6 of the Beta globin gene. In normal individuals, codons 5 and 6 comprise the nucleotides CCT GAG, respectively. However, in the affected individuals, there is an A to T point mutation in codon 6 resulting in the changed sequence, CCT GTG. Thus, enzymes such as Dde recognize and cleave DNA from the unaffected individual, but not DNA from the affected individual.

A third, and quite complicated technique, has recently been described by Landegren, et al.: A ligase-mediated gene detection technique. (Science 24 : 1077–1080, 1989). This technique is quite complicated because it involves the dual hybridization of both a probing sequence, bearing a tag such as an antibody tag, in combination with a second, labeled probing sequence. This technique relies upon the ability to hybridize two fragments in an adjacent position along a selected region of a DNA strand, such as a gene suspected of containing a particular mutation. The mutation is detected by the ability to ligate the probe bearing the mutation and tag to the separate probe bearing the label. Ligation will be achieved only where the mutation-bearing probe aligns in a position adjacent to the label-bearing probe. As one might imagine, such a technique could only be performed with great difficulty, involving many steps and is likely not practical in the case of a clinical laboratory application.

The present invention involves a dramatic improvement over the foregoing approaches to DNA analysis and relies in part on the PCR technique. The PCR technique, described in U.S. Pat. Nos. 4,683,202 and 4,683,195, involves a process for amplifying any desired specific nucleic acid sequence contained in a nucleic acid sequence within a nucleic acid molecule. The process includes treating separate complementary strands of the nucleic acid with an excess of two oligonucleotide primers, and extending the primers to form complementary primer extension products which subsequently act as templates for synthesizing the desired nucleic acid sequence. The steps of the PCR reaction may be carried out stepwise and simultaneously, and can be repeated as often as desired in order to achieve increased levels of amplification of the desired sequence. By this technique, the sequence of DNA between the primers on the respective DNA strands will be amplified selectively over the remaining portions of the DNA in the selected sample. The PCR technique therefore provides for specific amplification of a desired region of the DNA. Unfortunately, while the PCR technique itself can amplify desired regions, it cannot directly identify the nature of the sequences contained within such a region.

Accordingly, it is apparent that there is needed a new approach that is applicable to identifying DNA mutations, particular short mutations such as point mutations or insertions or deletions of short regions. In particular, there is needed a technique which has broad applicability to a wide variety of mutations, such as to point and other short mutations, which can be performed by a technician with minimal training and with minimal difficulty and complexity of manipulation. The present invention addresses these inadequacies in the art by providing such a technique which can generally be applied to any mutation having a known position or configuration and which can be performed simply with relatively few steps.

SUMMARY OF THE INVENTIONS

The present invention addresses these and/or other inadequacies in the prior art by providing a technique for detecting the presence or absence of a target DNA sequence within an identified region of a selected DNA molecule. The technique of the present invention relies in part on the PCR in vitro amplification procedure to amplify preferentially regions which contain the target sequence or, alternatively or in addition, to amplify selectively regions which do not contain the target sequence. In a general and overall sense, the key to the present invention is the use of a nucleic acid primer molecule which is capable of priming PCR amplification selectively from DNA which contains the sequence that is targeted, such as a point mutation, insertion, deletion, or the like.

In a broad sense, therefore, the present invention is directed to a method for detecting the presence or absence of a target DNA sequence within an identified region of a selected DNA molecule, wherein when the target is present in the region, it has an expected location and configuration therein. In the context of the present invention, the term "target DNA sequence" is intended to refer generally, but not exclusively, to variations, mutations and polymorphics. However, "target DNA sequences" generally refers to any sequence present in a selected DNA molecule wherein one desires to determine whether such a sequence is present in the selected molecule, such as in comparison to a reference DNA molecule.

In certain embodiments, the identified region of the selected DNA molecule will be a gene which is known or thought to include a particular mutation, such as a point mutation. The mutation that is targeted for analysis, when present in the gene, will have an expected location and configuration therein. By this is meant that the mutation will generally, but not always, have a known sequence, and will be present at a known location within the gene. Accordingly, by "configuration" is meant that the location of the mutation or target sequence, but not necessarily its sequence, known with respect to the surrounding sequences of the gene or other identified DNA region.

An example of such mutations which have been characterized to have an expected location and configuration are seen in diseases such as diabetes, sickle cell anemia, alpha and beta thalassemia, phenylketonuria, hemophilia, alpha 1-antitrypsin deficiency, acute intermittent porphyria, and possibly even diseases such as cystic fibrosis and Huntington's chorea. Furthermore, cancer oncogenes such as N-ras, K-ras, H-ras, Neu, or tumor suppressor genes such as p53 are known to have such mutations which contribute to the cancer development. In the case of sickle cell disease, the mutation involves the replacement of the sixth amino acid glutamate with valine through an adenine to thymine nucleotide switch. Similar mutations having expected locations and configurations are known in the art and are applicable to the present invention, and the present invention is applicable to such other mutations. Furthermore, additional mutations having expected locations and configurations will surely be characterized in time, and the present invention will be likewise applicable to such mutation as may be identified in the future.

As noted, the present invention involves an improvement to the PCR amplification technique. As is known in the art, PCR amplification involves generally the use of two separate primers which are capable of binding along the 3' regions of the DNA region to which one desires to amplify. While the present invention is preferably performed using two separate primers, this is not an absolute requirement in that through the practice of the invention one is attempting to determine whether the primers are capable of priming DNA synthesis from a selected DNA molecule. Accordingly, a first step of the present invention involves obtaining a nucleic acid primer molecule having a template binding region that is capable of hybridizing to a first strand of the selected DNA molecule at a binding position 3' of and adjacent to the expected location of such a target sequence within the DNA molecule. Thus, such primer molecules of the present invention have the ability to bind at a position of the DNA that is just 3' of the target sequence.

A novel aspect of the present invention, however, is that the primer molecule further includes at its 3' terminus and at a position adjacent to template binding region, a "target sequence complementary region" comprised of at least one nucleotide that is complementary to a corresponding nucleotide of the target sequence. Of course, where the sequence that is targeted is a point mutation, the "target sequence complementary region" will be a single nucleotide that is complementary to the point mutation. Thus, where a point mutation involves an adenine, or "A" residue, the primer molecule will include a thymidine or "T" residue, at its 3' terminus. Where longer insertions, deletions or alterations are to be detected, one may desire to include longer "target sequence complementary regions", such as, for example, one, two or even 3 or more nucleotides that are complementary to the targeted sequence. However, even in these embodiments, only a single nucleotide that is complementary to its corresponding nucleotide of the target sequence is required for successful practice of the invention.

A unique and even surprising aspect of the invention involves the inventors' finding that primers such as the foregoing are capable of priming selectively only on sequences which include the targeted mutation. Thus, where the selected DNA molecule does not include the target DNA sequence within the expected location and configuration, the primer will not function to prime DNA synthesis. Accordingly, a second step of the invention in its broadest sense involves determining the ability of the primer molecule to prime polymerase chain extension using the selected DNA molecules template, to detect the presence or absence of the target sequence within the selected DNA molecule.

In certain particular embodiments, the first nucleic acid primer molecule will include, at a position one to three nucleotides 5, of the target sequence complementary region, and positioned between the template binding region and the target sequence complementary region, a nonsense nucleotide on the selected DNA molecule. The inclusion of such a nonsense nucleotide into the primer sequence at a position between the template binding region and the target sequence complementary region provides for additional assurances that the first primer will not effectively prime DNA synthesis on templates which do not include a target sequence. That is, the inventors have found that the inclusion of a nonsense nucleotide will not appreciably inhibit the priming event so long as the 3' terminal nucleotide is complementary to the template. However, the inclusion of such a nonsense nucleotide provides additional advantages in that where the 3' terminal nucleotide is not complementary to its corresponding nucleotide along the template, the inclusion of the nonsense nucleotide provides an additive effect in terms of preventing the occurrence of an inadvertent priming event.

As noted, while one may employ simply a single primer such as the foregoing to detect the presence of the target sequence within the selected DNA molecule, one will generally desire to employ a second primer capable of priming synthesis on the second strand of the selected DNA molecule, so as to achieve PCR amplification of the region bearing the target, when such a target is present therein. Accordingly, in certain embodiments, determining the ability of the primer molecule to prime polymerase chain extension will include obtaining a second nucleic acid primer molecule having a second template binding region that is capable of hybridizing to the second strand of the selected DNA molecule at a binding position 3' of the expected location of such a target sequence, and determining the ability of the first and second primers to prime polymerase chain reaction synthesis of both strands of the DNA molecule, such an ability being indicative of the presence of the target sequence within the selected DNA molecule.

The second binding position on the second strand of the selected DNA molecule can be located at virtually any binding position 3' of the expected location of the target, so long as the chain extension can proceed from the first binding position to the second binding position, thus allowing PCR amplification. In that it has generally been found that the enzyme currently in use for PCR amplification, the Taq enzyme, can proceed up to 1,000 nucleotides, and perhaps even more, one could theoretically choose a second binding position that is up to 1,000 nucleotides removed from the first binding position. However, this will not generally be a preferred embodiment. Preferably, one will choose a second binding position that is 30 to 600, and more preferably 60 to 260, nucleotides removed from the first binding position.

In particular embodiments, determining the ability of the first and second primers to prime polymerase chain reaction synthesis along with selected DNA molecule will include steps of hybridizing the primers with the selected DNA molecule to form primed templates, subjecting the primed templates to polymerase chain extension to form polymerase chain extended products, and detecting the generation of polymerase chain extended products having a size corresponding to about the accumulative size of the first and second primers together with the distance between their respective primer binding positions along the DNA molecule. Thus, where primers of about 20 to 40 nucleotides in length are employed, and separate by about 100 nucleotides, the expected polymerase chain extension product will have a size of about 140 to about 180 nucleotides.

Of course, it will be appreciated that the primers may include DNA sequence regions located 5' of the binding region which will not take part in binding of the primer to the template, and such regions will be included in the calculations of the expected size of the PCR extended product.

In certain embodiments, the generation of polymerase chain extended products will be detected by subjecting the polymerase chain products to gel electrophoresis, such as agarose gel electrophoresis, and identifying products of the appropriate size, for example, by means of a label such as a radionuclide, fluorescence, or enzyme. However, where several cycles of synthesis are employed, it will generally be the case that the products can be detected directly by simply staining the gel with appropriate DNA staining reagents such as ethidium bromide.

While it is believed that one could successfully determine the ability of the first and second primers to prime PCR synthesis, for example, through the hybridization or use of radiolabeled nucleotides, one will generally desire to employ several cycles of synthesis, such as, 10 to 60 cycles, and more preferably 25 cycles of PCR synthesis.

In still further embodiments of the invention, one will desire to also determine the ability of the primer molecules to prime polymerase chain extension using a reference DNA molecule as template, wherein the reference molecule includes an identified region which has been characterized in terms of the presence of absence of the target sequence. Thus the reference DNA molecule will generally be DNA, such as genomic DNA, which includes the identified region, or gene, in a non-mutated form (e.g., a sequence known not to include the point mutation, insertion, deletion, etc.). Thus, such a reference molecule provides just that, a reference against which one can measure the priming activity of the unknown, selected DNA molecule. Where the selected DNA molecule is genomic DNA obtained from a patient suspected of having agenetic disease, the reference DNA molecule will generally be genomic DNA from an individual known not to have the mutation being targeted by the assay. In such embodiments, one will generally desire to simply compare the ability of the respective first and second primers to prime synthesis on the selected DNA in relation to the reference DNA.

However, in a still further aspect, one may desire to employ additionally further primers designed to prime synthesis selectively on the reference molecule and not on the selected molecule, if such a selected molecule does not contain the target sequence. In such embodiments, the method of the invention will further include obtaining a third nucleic acid primer molecule having a third template binding region that is capable of hybridizing to the first or second strand of the selected DNA molecule at a binding position 3' of and adjacent to the expected location of such a target sequence within the DNA molecule, the primer molecule further including at its 3' terminus at least one nucleotide complementary to the corresponding nucleotide on the reference DNA molecule.

Thus, rather than including at its 3' terminus a nucleotide complementary to the target sequence, as is the case in the first primer molecule, the third primer molecule will incorporate a 3' terminal nucleotide or nucleotides which are complementary to corresponding nucleotides which will be present when the target sequence is absent. Typically, this will mean that the third nucleic acid primer molecule will have a 3' terminal nucleotide(s) which is complementary to corresponding nucleotides of non-mutated or non-variant sequences.

In accordance with the invention, in contrast to the first primer, the third nucleic acid primer will prime synthesis on DNA molecules which do not include the target sequence, such as a reference DNA molecule, and will not prime synthesis on DNA molecules which have the target sequence. Accordingly, the third nucleic acid primer molecules will then be used to determine the ability to prime polymerase chain extension using either the selected or referenced molecules template, such an ability being indicative of the absence of the target sequence in the respective DNA molecule, whether it be the reference or selected molecule.

In certain embodiments, the third template binding region will simply correspond to the first template binding region, the of the third primer only difference between the first and third primers being the identity of their respective 3' terminal nucleotide or nucleotides.

Accordingly, as in the case of the first primer, one will generally desire to employ a fourth primer for use in connection with the third primer in order to determine the ability of the third primer molecule to prime polymerase chain extension along with the selected or reference molecule. In these embodiments a fourth nucleic acid primer is obtained having a fourth template binding region that is capable of hybridizing to the opposite strand from the third primer molecule at a binding position 3' of the expected location of such a target sequence, and determining the ability of the third and fourth primers to prime polymerase chain extension on both strands of the reference or selected DNA molecule, such an ability being indicative of the absence of the target sequence within their respective DNA molecule. For convenience, the fourth nucleic acid primer molecule can simply correspond or be equivalent to the second nucleic acid primer molecule, when the first and third parimers recognize the same strand.

As noted above, the present invention will have particular applicability to the detection of point mutations in DNA molecules. Thus, in certain embodiments, the present invention is directed to a method for detecting the presence of a point mutation within a selected gene of a selected DNA molecule wherein when said point mutation is present in the gene, it has an expected location and configuration therein. The method of this aspect of the invention will generally comprise the steps of (1) obtaining a nucleic acid primer molecule having a template binding region that is capable of hybridizing to a first strand of the selected DNA molecule at a binding position 3' of and adjacent to the expected location of the point mutation, the primer molecule further including at its 3' terminus and adjacent to the binding region a nucleotide that is complementary to the point mutation, and (2) determining the ability of the primer molecule to prime polymerase chain extension using the selected DNA molecule template, to detect the presence or absence of the point mutation within the selected DNA molecule.

In still further aspects, the invention concerns novel nucleic acid primer molecules for use in connection with polymerase chain extension for determining the presence or absence of a DNA sequence that has an expected location and configuration with an identified region of a selected DNA molecule. The novel nucleic acid primer of the invention has a template binding region that is capable of hybridizing to a first strand of the selected DNA molecule at a binding position 3' of and adjacent to the expected location of such a target sequence within the DNA molecule, the primer molecule further including at its 3' terminus and adjacent the template binding region a target sequence complementary region comprised of at least one nucleotide complementary region to a corresponding nucleotide of the target sequence.

In certain embodiments, the primer molecule further includes, at a position one to three nucleotides 5' of the target sequence complementary region, and positioned between the template binding region and the target sequence complementary region, a nonsense nucleotide that is not complementary to its corresponding nucleotides on the selected DNA molecule.

BRIEF DESCRIPTION OF THE DRAWINGS

In FIG. 1A, the primers are depicted in their hybridized position on a hypothetical template which includes the variant. Depicted in FIG. 1B is the primed first cycle synthesis employing the original mutated DNA molecule as the respective template for the primers. In FIG. 1C is shown a second round of synthesis wherein elongated chains from the first cycle of synthesis are reacted with additional primers and polymerase enzyme to achieve a second cycle of synthesis with the first cycle elongated chains serving as templates.

Figure 1A:
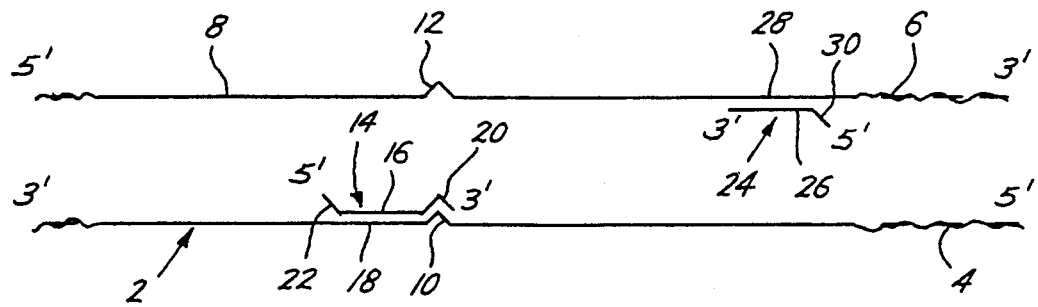
FIGS. 1A-C depict the PCR in vitro amplification of DNA through the use of primers prepared in accordance with the present invention. The DNA depicted in FIGS. A-C includes a sequence variant that is detected through the practice of the invention.
Figure 1B:
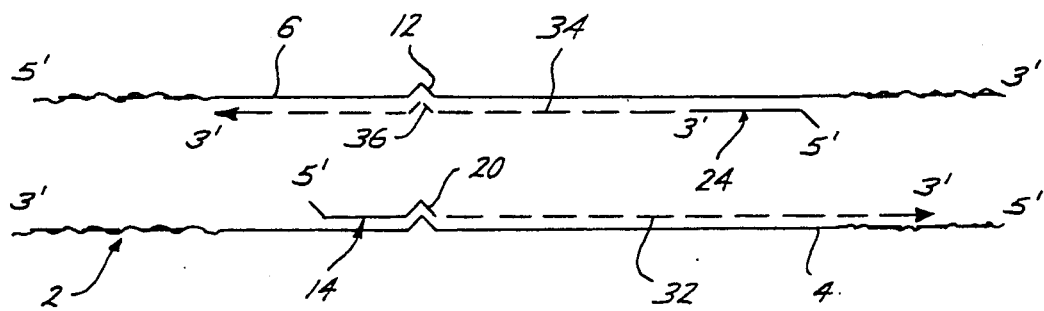
Figure 1C:
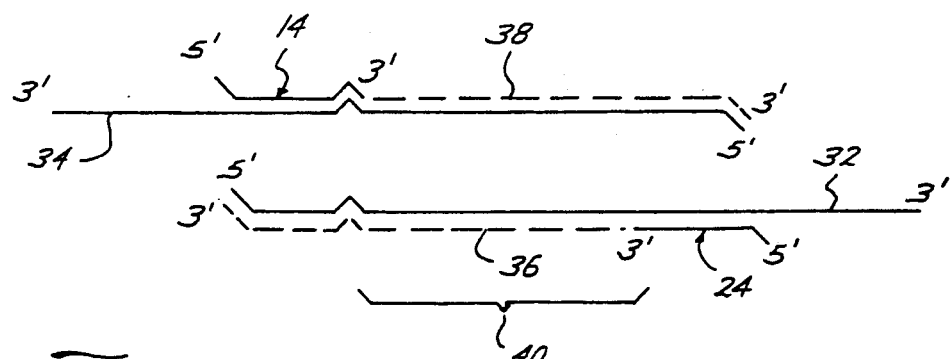
Figure 2:
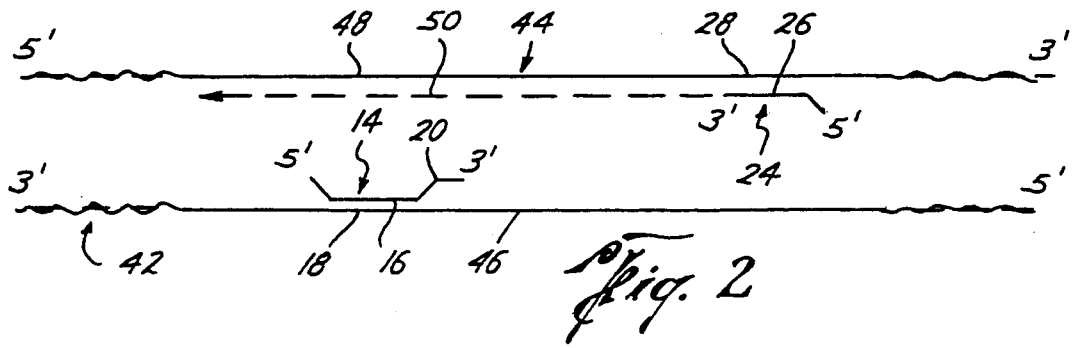

Shown in FIG. 2 is the application of the same primer shown in FIG. 1 to a DNA molecule which does not include the mutation. As is depicted in FIG. 2, the primers are unable to achieve amplification of the desired region.

Figure 3A:
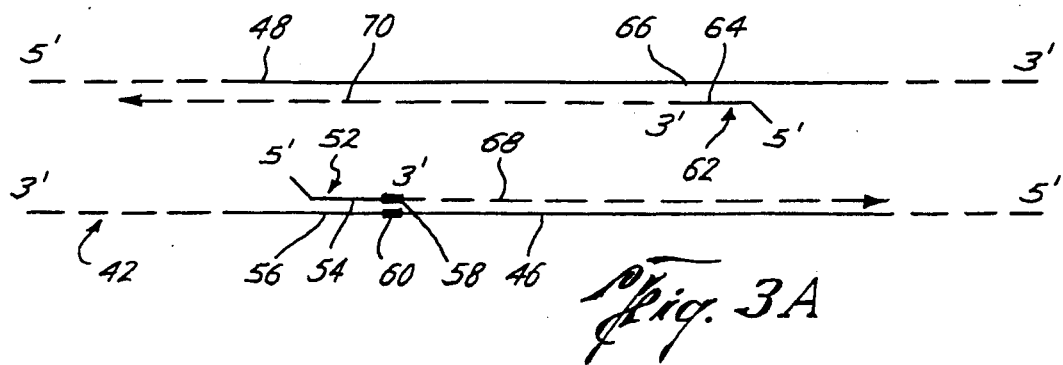
Figure 3B:
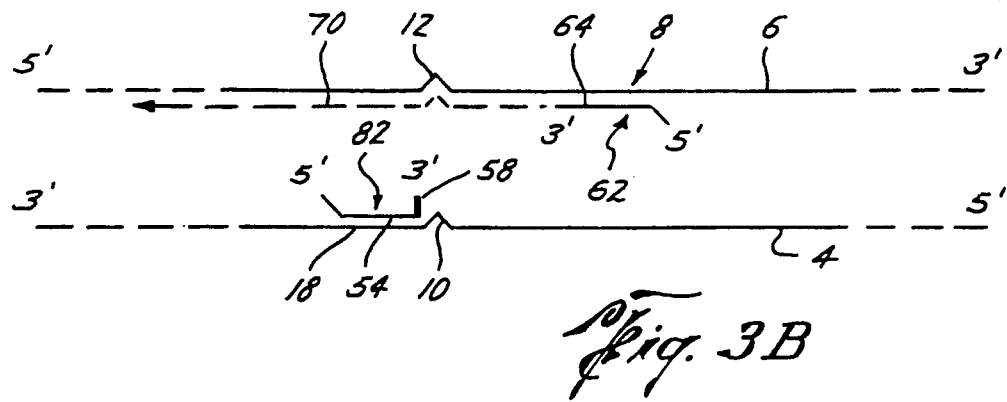

FIGS. 3A-B depict the preparation of primers that will specifically prime synthesis on a wild type molecule which does not incorporate the target sequence (FIG. 3A) as well as application of the wild type-directed primers to a selected DNA molecule that does incorporate the target sequence (FIG. 3B). As is depicted in FIG. 3B, the wild type-directed primers are unable to support amplification of the desired region of the selected primer which bears the target sequence.

Shown in FIGS. 4A-D is the application of primers to determine the presence of absence of a point mutation in a selected DNA or will type DNA molecule.

Figure 4A:
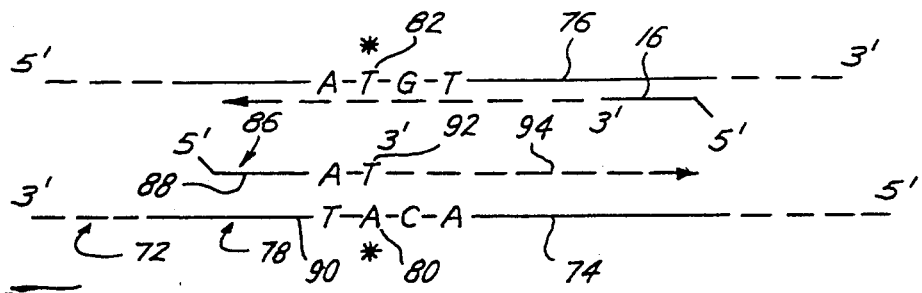
Figure 4B:
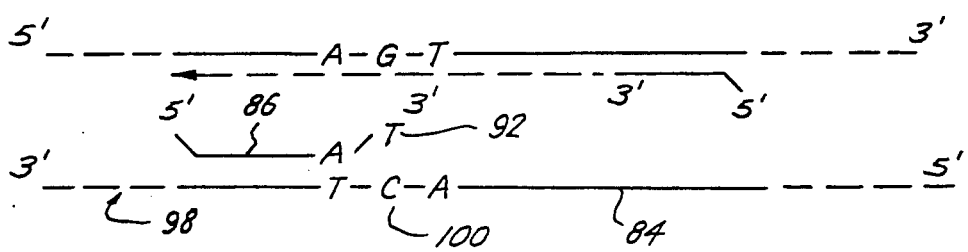
Figure 4C:
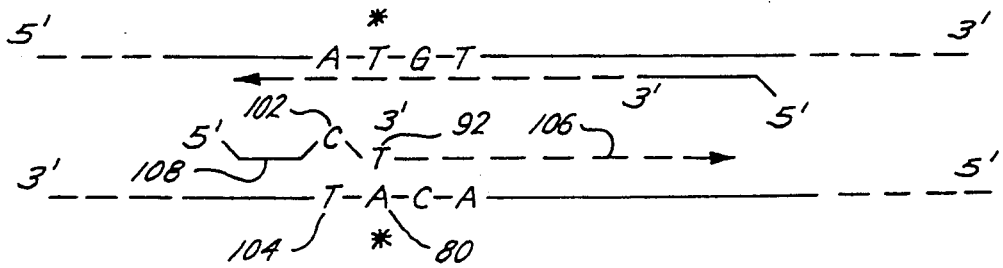
Figure 4D:
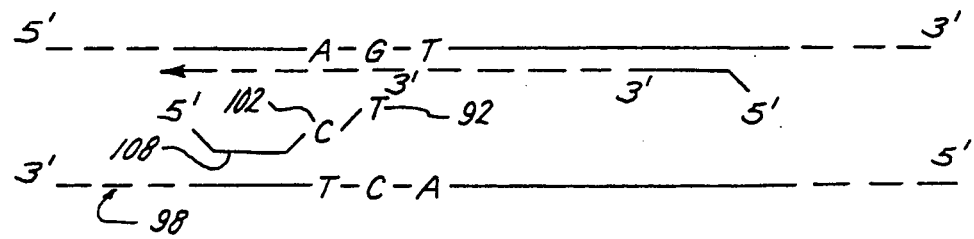

Also shown in FIGS. 4C–D is the incorporation of a nonsense nucleotide which provides further advantages in accordance with the invention.

DETAILED DESCRIPTION OF THE PREFERRED EMBODIMENTS

The present invention relates generally to the preparation and use of nucleic acid primers in the detection of sequence variations, mutations and the like, in DNA samples. Primers are DNA molecules which are employed to "prime" the synthesis or copying of a "template" DNA strand by a DNA polymerase enzyme into a complementary strand. The newly generated complementary strand will elongate from the primer into a new strand that remains bound or hybridized to the template strand unless denatured.

In nature, DNA polymerases are required in order to catalyze DNA synthesis prior to cell division, providing an "extra", exact copy or replica of a cell's genomic DNA molecule to the daughter cells. The cell's entire DNA complement is copied prior to cell division, through copying of each strand into a complementary strand. Each DNA strand has a defined polarity, a "3' direction" and a "5' direction", governed by the head-to-tail arrangement of the pentose-phosphate backbone. The ribose molecule portion of the pentose-phosphate backbone has a 5' carbon d a 3' carbon linked to adjacent ribose molecules through aphosphate molecule. Furthermore, complementary DNA strands run in an "anti-parallel" direction with respect to each other, with one strand running in an opposite direction of its complement. Thus, a 3' direction on one strand corresponds to a 5' direction on the complement.

In order to achieve the enzymatic copying of a DNA strand, whether in a cell (in vivo) or in a test tube (in vitro), the DNA polymerase enzyme must have a starting point from which to begin its synthesis. This starting point is the 3' terminus of the "primer" or "priming strand". The primer is annealed to the template strand at a position at which DNA synthesis begins. During DNA replication, the DNA polymerase enzyme begins its copying of the template strand at the 3' end of the priming strand and forms a covalent phosphate linkage with the 5' carbon of the growing chain. Due to the fact that DNA replication has a 3' to 5' polarity of elongation, synthesis proceeds in a 3' direction with respect to the strand that is being copied (the template).

The present invention relies in part on the observation that in order for a primer molecule to successfully "prime" DNA synthesis from a template, the 3'-terminal nucleotide of the primer must be capable of base pairing with the template. That is, the 3'-terminal nucleotide of the primer must, in essence, be capable of "lying flat" against the template strands and remain in a proper configuration for a sufficient length of time to achieve a priming of the DNA polymerase enzyme's ability to proceed with synthesis. Thus, if a particular DNA molecule that one attempts to employ as a primer is otherwise capable of annealing to the template, but does not have a 3'-terminal nucleotide that can "lie flat" against the template for a sufficient period of time, the DNA molecule cannot properly function as a primer. Such a "primer" molecule which does not have a 3'-terminal nucleotide that is capable of hybridizing with or otherwise "lying flat" against the template strand is said to have a "3'-terminal flap" or a 3,-terminus which "flaps away" from the template.

The present invention takes advantage of this observation to provide a simple and reliable means for detecting the presence or absence of a particular DNA target sequence within a gene or other region of a selected DNA molecule. In a general sense, this is achieved by providing a primer molecule that will successfully prime DNA chain elongation only on DNA template molecules to which it can both hybridize and having a 3' terminus that will base pair with or otherwise lie flat against the template (i.e., where the template contains a nucleotide that is complementary to the 3' pair with the 3' terminus of the primer when the primer is annealed to the template).

When these conditions are met, the primer will successfully prime chain elongation. However, if the template does not include a complementary nucleotide in the 3' terminal position, the primer will not prime chain elongation. This provides the ability to prepare primers that will successfully prime chain synthesis only where the template strand contains a particular expected variant or mutation, but will not prime synthesis on control or "wild-type" templates that do not include the mutation. Alternatively, it provides the ability to prepare primers that will prime chain elongation only of templates that do not include the mutation or variant, and will not prime synthesis of templates that include the variant or mutation.

The only requirement for preparing and employing primers of the present invention, is that one must know the approximate sequence of the region of the template strand that one is seeking to investigate, as well as the expected location or "configuration" of the variant or mutation "target, when it is present. This knowledge allows one to prepare primers that will hybridize and prime only under the selected conditions. While not absolutely necessary it will be desirable to know the expected nucleotide sequence of the variant or mutation. This allows one to employ a single primer that can be used universally, e.g., where one is seeking to develop an assay for screening for a particular mutation or genetic abnormality. Of course, while many genetic diseases involve mutations that occur at an expected site within a gene, it is not always the case that such mutations will involve the same nucleotide chain, insertion, etc.

The primer molecule that is employed for detecting the sequence variance is therefore preferably constructed such that it includes at its 3' terminus at least one nucleotide that is complementary to a corresponding nucleotide of the target sequence located on the intended template strand of the DNA molecule that is selected for analysis. For the purposes of the present disclosure, the 3' terminal region of the primer that is complementary to the sequence variant will be referred to as the "target sequence complementary region" or TSCR. Where the target sequence or targeted variant is a single nucleotide (such as a point mutation), the TSCR will comprise a single nucleotide that is complementary to the point mutation. However, where the targeted variant involved multiple nucleotides, the TSCR may include more than one complementary nucleotides.

The TSCR portion of the primer, located on the 3' terminus of the primer, is generally positioned immediately adjacent to and 3' of a template binding region (TBR) that is capable of hybridizing to the template strand at a primer binding position (PBP) 3' of an adjacent to the expected location of the target sequence within the template molecule. The TBR will generally be from about 7 to 25 nucleotides in length but there is no reason why it cannot be longer where desired. All that is required is that the primer have a TBR sequence that is sufficiently complementary to the PBP so as to hybridize to the template under the hybridization conditions selected for the assay. Thus, one will generally desire to employ a TBR sequence that is at least 15 nucleotides in length; the upper limit is not believed to be particularly crucial.

In certain embodiments, advantages will be realized through the inclusion of a "nonsense" nucleotide, positioned between the TSCR and the TBR. Such a nonsense nucleotide is a nucleotide that is not complementary to its corresponding nucleotide on the templates, regardless of whether the template includes the target sequence or not. The reason for including such a nonsense nucleotide, usually at a position 1 to 3 nucleotides 5' of the TSCR, is in order to increase the degree of "3' terminal flap" that will occur when the target sequence is not present. That is, when a non-hybridizing "nonsense" nucleotide is included in the primer construct, and a target sequence such as a point mutation is not present on the template, there will be at least two mismatched bases at the 3' end of the primer. This will ensure that the priming event will not occur and prevent the low grade "leakage" of priming which may occur when only the 3' terminus is mismatched. Surprisingly, the inventors have found that such a construct will nevertheless successfully prime chain elongation when the target sequence is present.

A third feature which one may wish to include in the primer construct is a region 5' of the TSCR that does not hybridize with the template. The inclusion of such a region is optional in that it will not take part in the elongation reaction. Since such a region does not take part in the elongation reaction, its length is not particularly crucial, so long as it is not so large as to prevent the complementary nucleotides from hybridizing therewith. Reasons for incorporating such a 5' terminal non-binding region include generally the ability to incorporate a desired secondary sequence, such as a particular restriction enzyme recognition site or ligation site, or even to form a secondary priming site. Other considerations include the use of the noncomplementary region in purification steps or for labeling and detection.

Thus, primers in accordance with the present invention for performing an embodiment of the assay will typically have a configuration which can be depicted as follows:

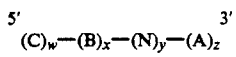

wherein C represents nucleotides that are not complementary to the template strand, with w equal to zero or a positive integer limited only by an overall primer to hybridize to the target DNA strand; B represents the template binding region of the primer, with nucleotides which are complementary to the template binding position 3' of and immediately adjacent to the expected location of the target sequence if present, with x generally equal to at least 10 to 15; N represents a nonsense nucleotide, that is not complementary to its corresponding nucleotide on the template, with y equal to zero or one; and A represents the TSCR, with z ranging from one up to the length of the target sequence.

Primers such as the foregoing are thus employed to determine their ability to prime chain elongation on a selected template suspected of carrying a particular variance. In general, the ability of such primers to initiate chain elongation can be ascertained in a variety of manners. For example, one can determine the ability to incorporate radioactive nucleotides, fluorescent or enzyme labels into elongating chains using the primers. Alternatively, one could prepare labeled hybridization probes for detecting elongated product, e.g., by filter paper hybridization. However, the preferred method for determining the priming capability of the foregoing primers is to employ them in connection with the PCR or in vitro DNA sequence amplification.

In PCR amplification, two separate primers are routinely employed, one for priming synthesis along one direction on one strand, and a second primer for priming chain elongation along the complementary strand in the opposite direction, starting from a position downstream the priming position of the first primer.

After a first cycle of synthesis, subsequent cycles of elongation are typically performed in order to achieve sequence amplification. This is done by dissociating elongated chains from their original templates, and reinitiating chain extension on the previously elongated products through the inclusion of excess primers in the reaction mixture. By performing cycles of chain extension, dissociation and primer annealing, one achieves sequence amplification of the particular sequence which extends between the two primers. In connection with PCR embodiments of the present invention, it will generally be adequate for most applications to perform 10 to 60 cycles of synthesis, with 25 cycles being preferred.

It is of interest to note that the size of the product of such PCR amplification will correspond to about the cumulative size of the first and second primers together with the distance between their respective binding positions along the DNA molecule. This is because after a first cycle of chain elongation, subsequent cycles of synthesis for the most part involve templates whose 5' termini are defined by the 5' termini of the respective primers employed.

Accordingly, where one desires to employ primers of the present invention in connection with the PCR technique, a second primer will typically be preferred. It will generally be the case that the second primer will be capable of priming chain elongation on its template regardless of the presence or absence of the target sequence. The reason for this is that where comparative assay are used, one will desire to keep the differences between control and experimental at a minimum. In connection with the present invention, a TSCR is incorporated into only one of the primer pairs employed in an assay. Furthermore, the second primer will typically be designed to initiate chain elongation at a position sufficiently removed from the first primer so that the amplification product, if any, is of a size that is distinct from the cumulative size of the starting primers. (This is due to the fact that the starting primers, as well as some cross-linking between primers, can often be observed as background following gel electrophoresis of the extension products).

In that the assay procedure of the present invention is directed to the detection of sequence variants, it will generally be of some advantage to compare the ability of the foregoing primers to prime chain extension on the selected DNA molecule, to their ability to prime a "reference" molecule that has been previously characterized in terms of the presence or absence of the target sequence. Typically, the reference molecule will simply be genomic DNA isolated from normal individuals that have been determined not to carry the particular mutation on either allele. However, other possible reference molecules include wild type viruses, phage, bacterial genomic DNA, synthetically prepared oligonucleotide strands or any other source of DNA which does not contain variant sequences.

Still further advantages, e.g., in terms of specificity and/or selectivity, may also be realized through the preparation and use of primers that will preferentially prime chain elongation on "wild-type" or reference DNA molecules. Such primers, instead of incorporating a 3' terminal TSCR, include a 3' terminal region that is complementary to the nucleotide(s) that occupy the position(s) on the template strand that would have been occupied by the target sequence if it were present.

Such primers, which will be referred to herein as third primers, will therefore have a template binding region that is capable of hybridizing to the first and second strand of the selected DNA molecule at a binding position 3' of and adjacent to the expected location of the target sequence and will further include at its 3' terminus at least one nucleotide complementary to the corresponding nucleotides on a reference molecule which replace the position held by the target sequence when it is not present. Such a 3' terminal region will be referred to herein as a wild type sequence complementary region, or WTSCR, to refer to the 3' terminal nucleotide or nucleotides that are complementary to corresponding nucleotide(s) present in "wild-type" DNA molecules, i.e., when the targeted variant or mutation is absent.

Of course, as with primers bearing the TSCR, where one desires to employ the invention in connection with in vitro amplification with a third primer bearing a WTSCR, one will typically prepare a complementary strand primer for priming synthesis from the complement of that recognized by the third primer. These complementary strand primers ("fourth" primer) may simply correspond to the second primer, discussed above (e.g., where the first and third primers are directed to the same strand). Alternatively, the fourth primer may be directed to a distant binding position. In any event, the fourth primer is designed to incorporate a template binding region that is capable of hybridizing to the opposite strand from that recognized by the third primer, at a binding position 3' of the expected location, whether present or absent, of the target sequence. As with successful priming with the first/second primer, successful priming with the third/fourth primers will generate a fragment having a predictable approximate length.

Regardless of whether one employs the first/second primer set, or third/fourth primer set, and regardless of how the selected test or reference DNA is employed for analysis, the assay itself will preferably be preformed essentially as described in U.S. Pat. Nos. 4,683,202 or 4,683,195. In general, this involves first obtaining the DNA sample to be tested, typically genomic DNA such as might be isolated from peripheral blood, epithelial cells, cytology specimens or tissue biopsies by a method such as proteinanse K digestion and phenol/chloroform extraction (see, e.g., Ausubel, et al.: Current Protocols in Molecular Biology, Chapter 2, Sections 1 and 2. Greene Publishing Assoc. and Wiley-Interscience, New York, 1987).

Preferably synthetic oligonucleotides of 15 to 20 nucleotides in length are prepared by any suitable method to match the normal genetic sequence with all anticipated variants or mutations in the sequence at the 3' terminus. A nonsense mutation may be incorporated one or two nucleotides 5' of the 3' terminus if accentuation of the degree of 3' terminal flap is desired. The specific nucleic acid sequence produced is complementary to the normal control sequence or the suspected mutated sequence. Since the genomic DNA is double stranded, it is necessary to separate the two strands prefereably by heat denaturation at 95° C. for five minutes, buy any suitable method for strand separation may be used (Cold Spring Harbon Symposia on Quantitiative Biology, Vol. XLIII: DNA replication and recombination, Kuhn, B, et al.: DNA helixes. New York, Cold Spring Harbor Laboratory, pp. 63-67, 1978). The amplification process is preferably as described in U.S. Pat. Nos. 4,683,202 and 4,683,195. Specifically one microliter of DNA is added to 10 microliters of a 10x reaction buffer containing 100 mM Tris-HCL pH 8.3 (at 25° C.), 500 mM KCL, 15 mM MgC12, 0.1% (w/v) gelatin (Sigma, St. Louis, Mo.); 200 micromolar of deoxynucleotides (dATP, dCTP, dGTP, and dTTP): 1.0 micromolar of the primer complementary to the sequence variant; 1.0 micromolar of the primer for the opposite strand; 2.5 units of Taq DNA polymerase; and double distilled sterile water to reach a total volume of 100 microliters. The mixture is amplified as follows: denaturation at 95° C. for 1.5 minutes, annealing at 50° C. for 2 minutes, and extension at 72° C. for 1 minute for 25 or more cycles. However, specific times and temperatures for each amplification step should optimized for each primer construct.

After amplification, 10 microliters of the amplified reaction is electrophoresed on an agarose gel selected for clear separation of the expected amplified product with the appropriate marker for a control [e.g., 4% Nusieve agarose el (FMC Bioproducts, Rockland, Me.) and Phi X174 (BRL, Bethesda, Md.) as the marker at 75 volts for approximately 45 minutes to separate a amplified product between 100 and 300 nucleotides]. The gel is strained by ethidium bromide for 15 minutes, rinsed in distilled water for 10 minutes and visualized under UV light for the presence of the expected amplified product. For confirmation, the gel is then transferred to a filter by The Southern technique and hybridized with the appropriate confirmatory probe. (Maniatis, et al.: Molecular Cloning, Cold Spring Harbor, pp. 382-390, 1982).

As noted above, the present invention will have particular applicability in the detection of point or other relatively short mutations in DNA. This is because prior to now, there have been virtually no readily applicable techniques, short of actual sequence analysis, for detecting relatively short mutations such as these. For application in connection with these mutations, the principal requirement is that the mutation occur in an expected location.

Representative mutations of such a nature to which the present invention will find particularly applicability include acute intermittent porphyria which has a quanine to adenine mutation in the last position of exon 12 of the porphobilonogen deaminase gene (Grandchamp, et al., Nucleic acid Research 17(16), 6637-49, 1989), osteogenesis imperfecta IV which has a proline to alanine switch in position 384 of the collagen COL1A1 gene (Marini, et al.: J. Biol. Chem. 264(20):11893-900, 1989), colon carcinoma which has K-ras codon 12 mutations converting glycine glycine to aspartinine, serine, valine, or cyteseine (Bos, et al., Nature, 327:293-7, 1987), hemoglobin C which has a quanine to adenine, hemoglobin S which has a replacement of the sixth amino acid, glutamate by valine by an adenine to thymine nucleotide switch (Siki, et al.: Analysis of enzymatically amplified beta-globin and HLA-DQ alpha DNA with allele-specific oligonucleotide probes. Nature 324:163-6, 1986), diabetes due to a point mutation in the insulin receptor gene with an arganine to serine mutation (Yoshimasa, et al.: Insulin-resistant diabetes due to a point mutation that prevents insulin proreceptor processing. Science, 240:784-7, 1988), and famial hyperchlolesterolemia on cause of which is a point mutation of the low density lipoprotein receptor gene which changes serine 156 to leucine (Hobbs, et al.: Evidence for a dominant gene that suppressed hyperchloesterolimia in a family with defective low density lipoprotein receptors. Journal of Clinical Investigation 84:656-64, 1989).

The examples are intended to illustrate a manner of practicing the invention, but are not intended to limit the use of the invention in any way. The first example demonstrates how the invention may be applied in the design of primers to distinguish normal alleles of the beta-globin gene from sickle cell alleles and hemoglobin C allleles, and identifies a variety of useful primers. The following primers can be used for detection of a hemoglobin C mutation in a beta-globin allele:

—GACTCCTA (wherein the dashed lines represent, e.g., non-hybridizing nucleotides)

In this primer, the last nucleotide adenine represents a point mutation responsible for hemoglobin C that is not present on the normal beta globin gene. The remainder of the primer is composed of sequences complementary to the beta-globin gene for a primer of 20 nucleotides in length. However an alternative primer construct may be desired which places a nonsense mutation by the point mutation to further accent the degree of 3' terminal flap:

—GACTCCGA or

—GACTCGTA

The following primer can be used for detection of a particular hemoglobin S mutation:

—GACTCCTGT

In this example, the last nucleotide, thymine, represents the point mutation responsible for sickle cell anemia. However, an alternative construct with a nonsense nucleotide placed one nucleotide 5' to the 3' terminus is as follows:

—GACTCCTCT or

—GACTCCGGT ,

Furthermore, the following primer can be used to determine the presence of the normal beta-globin allele:

—GACTCCTG

In all three instances the primer used for amplification of the opposite strand is located at a distance preferably 70 to 150 nucleotides 3' from the above primers, but may be more, and represents complementary sequences of 20 nucleotides in length to the opposite strand of the beta-globin gene.

In terms of DNA specimens, extraction and preparation, human DNA specimens may be collected from any source but preferably from epidermal scrapings or peripheral blood. DNA is extracted by standard technique of proteinase K digestion and phenol/chloroform extraction (Ausubel, et al. Eds.: Current Protocols in Molecular Biology. Chapter 2, section 1 and 2. Greene Publishing Assoc. and Wiley-Interscience, New York, 1987).

For each specimen three small Eppindorf tubes are prepared such that each will use a different primer construct: 1) normal beta-globin primer set, 2) sickle cell primer and a primer for the opposite strand with normal beta-globin complementary sequences, 3) primer for hemoglobin C and a primer for the opposite strand with normal beta-globin complementary sequences. Since the genomic DNA is double stranded it is preferable to separate the two strands by heat denaturation at 95° C. for five minutes in a heat block. To each tube one microliter of DNA is added followed by 10 microliters of a 10x reaction buffer containing 100 mM Tris-HCL pH 8.3 (at 25° C.), 500 mM KCL, 15 mM MgC12, 0.1% (w/v) gelatin (Sigma, St. Louis, MO); 200 micromolar of deoxynucleotides (dATP, dCTP, dGTP, and dTTP); 1.0 micromolar of the primer complementary to the normal beta-globin gene (tube #1), sickle cell mutation (tube #2), and hemoglobin C mutation (tube #3); 1.0 micromolar of the primer complementary to the normal beta-globin opposite strand; 2.5 units of Taq DNA polymerase; and double distilled sterile water to reach a total volume of 100 microliters. The Eppindorf tubes are placed in a heat block and amplified as follows: denaturation at 95° C. for 1.5 minutes, annealing at 50° C. for 2 minutes, and extension at 72° C. for 1 minutes for 25 cycles.

Ten microliter aliquots from each tube are removed and loaded preferably onto a 4% Nusieve agarose gel with lane one of the gel containing the marker phi X174 as a control for size fragmentation. Lane two, e.g., would contain the aliquot from the normal beta-globin primer set, lane three an aliquot from the sickle cell primer and lane four would contain the aliquot from the hemoglobin C primer. The gel is electrophoresed for 45 minutes at 75 Volts. The gel is stained with ethidium bromide for 15 minutes then rinsed for 10 minutes in distilled water. Under ultraviolet fluorescent examination the gel is examined for the expected size fragment for each primer set (expected size equals the length of both primers plus the distance between the primers) as determined in reference to the phi X174 size marker.

Interpretation of the results would be as follows. The presence of a band in lane two would be indicative of the presence of a normal beta-globin allele. If no band is apparent in lanes three or four then only normal beta-globin alleles are present. However if a band of the expected size is also present in lane three then the specimen is consistent with sickle trait (hemoglobin A and hemoglobin S) or if a band is present in lane four then the specimen is consistent with a carrier trait for hemoglobin C (Hemoglobin A and Hemoglobin C). If only a band in lane three is present then the specimen is consistent with sickle cell disease (Hemoglobin S and Hemoglobin S). If a band is present in both lanes three and four but not lane two then the specimen is consistent with hemoglobin SC.

Example II, below, demonstrates how the present invention may be applied for design of primers to distinguish acute intermittent porphyria. The primer construct for the normal porphobilinogen deaminase gene would consist of around 20 nucleotides complementary to the normal strand (—GCACCTG). The mutated primer would consist of the same sequences except for the 3' terminus (—GCACCTA) which corresponds to the site of mutation responsible for the disease (Grandchamp, et al.: A point mutation G to A in exon 12 of the porphobilinogen deaminase gene results in exon skipping and is responsible for acute intermittent prophyria. Nucleic acids research 17:6637–49, 1989). As in example I a primer construct can be made with an additional nonsense mutation to increase the degree of 3' terminal flap (—GCACCGA). The primer used for amplification of the opposite strand is located at a distance preferably 70 to 150 nucleotides 3' from the above primers, but may be more, and represents complementary sequences of 20 nucleotides in length to the complementary to the opposite strand of the porphobilinogen deaminase gene.

Human DNA specimen may be collected from any source but preferably from epidermal scrapings or peripheral blood. DNA is extracted by standard technique of proteinase K digestion and phenol/chloroform extraction (Ausubel, et al. Eds.: Current Protocols in Molecular Biology. Chapter 2, section 1 and 2. Greene Publishing Assoc. and Wiley-Interscience, New York, 1987).

For each specimen two small Eppindorf tubes are prepared, each preferably using a different primer construct: 1) normal porphobilinogen deaminase gene primer set, and 2) mutated primer and a primer for the opposite strand with complementary sequences. Since the genomic DNA is double stranded, it is desirable to separate the two strands by heat denaturation at 95° C. for five minutes in a heat block. To each tube one microliter of DNA is added followed by 10 microliters of a 10x reaction buffer containing 100 mM Tris-HCL pH 8.3 (at 25° C.), 500 mM KCL, 15 mM MgCl2, 0.1% (w/v) gelatin (Sigma, St. Louis, Mo.); 200 micromolar of deoxynucleotides (dATP, dCTP, dGTP, and dTTP); 1.0 micromolar of the primer complementary to the normal porphobilinogen deaminase gene (tube #1) and mutated primer set (tube #2); 1.0 micromolar of the primer complementary to the normal beta-globin opposite strand; 2.5 units of Taq DNA polymerase; and double distilled sterile water to reach a total volume of 100 microliters. The Eppindorf tubes are placed in a heat block and amplified as follows: denaturation at 95° C. for 1.5 minutes, annealing a 50° C. for 2 minutes, and extension at 72° C. for 1 minute for 25 cycles.

Ten microliter aliquots from each tube are removed and preferably loaded onto a 4% Nusieve agarose gel with lane one of the gel containing a marker, e.g., phi X174, as a control for size fragmentation. Lane two would contain the aliquot from the normal porphobilinogen deaminase primer set and lane three, the aliquot from the mutated primer set. The gel is electrophoresed for 45 minutes at 75 Volts. The gel is stained with ethidium bromide for 15 minutes then rinsed for 10 minutes in distilled water. Under ultraviolet fluorescent examination the gel is examined for the expected size fragment for each primer set (expected size equals the length of both primers plus the distance between the primers) as determined in reference to the phi X174 size marker.

Interpretation of the results is as follows: The presence of a band in lane two would indicate the presence of a normal porphobilinogen allele. If no band is apparent in lane three then only normal alleles are present. However, if a band of the expected size is also present in lane three or only a band in lane three is present then the specimen is consistent with acute intermittent porphyria.

The present invention may also be applied for design of primers to distinguish one cause of diabetes due to a mutation in the insulin proreceptor. The primer construct for the normal insulin proreceptor gene would consist of around 20 nucleotides complementary to the normal strand (—CGGAAACGCAGG) and for the mutated primer it would consist of the same sequences except for the 3' terminus (—CGGAAACGCAGT) which corresponds to the site of mutation. An alternative primer construct could be made with an additional nonsense mutation to increase the degree of 3' terminal flap (—CGGAAACGCACT). The primer used for amplification of the opposite strand is located at a distance preferably 70 to 150 nucleotides 3' from the above primers, but may be more, and represents complementary sequences of 20 nucleotides in length to the complementary to the opposite strand of the insulin proreceptor gene.

The assay is performed essentially in the same manner as described in example number II. Interpretation of the results is as follows. The presence of a band in lane two would indicate the presence of a normal insulin proreceptor allele. If no band is apparent in lane three then only normal alleles are present. However if a band of the expected size is also present in lane three then the specimen is consistent with a mutation of the insulin proreceptor gene and a carrier state. If only a band in lane three of the expected size is present, then both alleles are mutated and this is consistent with a form of diabetes.

It is believed that the present invention may be more particularly described by reference to the various included drawings. Referring first to FIG. 1A is shown a selected DNA molecule 2 having a first strand 4, running in a 3' to 5' direction (left to right) and a second strand 6 running in a 5' to 3' direction (left to right). The second strand 6 is a complement of the first strand 4 of the selected DNA molecule 2. Within the selected DNA molecule 2 is an identified region 8, such as a selected gene. The identified region 8 of the selected DNA molecule 2 further includes a target sequence 10 on the first strand 4, and a complement of the target sequence 12 on the second strand 6. The target sequence 10, 12 will typically be a mutation, such as a point mutation, insertion, or the like.

Also shown in FIG. 1 is a nucleic acid primer molecule 14 having a template binding region 16 that is capable of hybridizing to the first strand 4 of the selected DNA molecule 2 at a binding position 18 that is 3' of and adjacent to the expected location of the target sequence 10. The primer molecule 14 will further include at its 3' terminus and adjacent the template binding region 16, a target sequence complementary region 20 comprised of at least one nucleotide complementary to a corresponding nucleotide of the target sequence 10. The primer molecule 14 may optionally include a 5' region 22 which does not hybridize with the template 4.

For use in connection with PCR in vitro amplification techniques, a second primer 24 is provided. The second primer 24 is capable of hybridizing to the second strand 6 by means of a second template binding region 26 that is complementary to a second binding position 28 that is located on the second strand 6 at a position 3' of the expected location of the target sequence 12. The second primer molecule 24 may also optionally include a 5' region 30 that will not hybridize to the template 6. The second binding position 28 is typically selected such that the separtion from the first binding sequence 18 is sufficient to provide an amplification product that is distinguishable from the cumulative size of the primers 14, 24.

Shown in FIG. 1B is the same DNA molecule 2 and associated primers 14, 24 which has been treated with a DNA polymerase, such as taq polymerase, in order to achieve elongation of newly synthesized DNA strands 32, 34. Synthesized strand 32 is therefore a complement of the first strand 4 and synthesis proceeds in a 5' to 3' direction (left to right). In contrast, newly synthesized strand 34 is a complement of the second strand 6, and synthesis of strand 34 also proceeds in a 5 to 3 direction (right to left). Newly synthesized strand 34 will further include a complement 36 of target sequence 12. Of course, newly synthesized strand 32, by virtue of its covalent attachment to first primer 14, will include the target sequence complementary region 20.

Shown in FIG. 1C are elongated chains 32 and 34 following the termination of chain elongation and subsequent dissociation of elongated chains from the original templates 4, 6. To achieve a second cycle of synthesis elongated chains 32, 34 are hybridized with an excess of primers 14 and 24 and chain elongation initiated by the action of DNA polymerase. As depicted in FIG. 1C, this results in the generation of newly elongated chains 36 and 38. However, the size of newly synthesized chains 36 and 38 will represent a size corresponding to about the cumulative size of the first and second primers 14, 24, together with the separation distance 40 between their respective binding positions along the DNA molecule 2. Furthermore, as can be seen from FIG. 1C, all subsequent DNA chains generated by subsequent cycles of synthesis using the elongated chains as templates will be limited to this overall length. Thus, amplification is detected by detecting the generation of polymerase chain extended products having a size corresponding to about the cumulative size of the first and second primers together with the distance between their respective primer binding positions.

Turning now to FIG. 2A is shown a reference DNA molecule 42 having an identified region 44 which corresponds to the identified region 8 of the selected DNA molecule 2, except for the absence of the target sequence 10, 12. The reference DNA molecule 42 includes a first strand 46, extending in a 3' to 5' direction (left to right) and a second strand 48 extending in a 5' to 3' direction (left to right). When the reference DNA molecule 42 is treated with first and second nucleic acid primers 14, 24, their respective template binding regions 16, 26 recognize and hybridize to their respective template binding regions 18, 28 within the identified region 44. However, due to the absence of target sequence 10 the 3' terminal target sequence binding region 20 of primer 14 will "flap away" from the template 46. Thus, upon addition of a DNA polymerase enzyme only primer 26 is capable of priming chain elongation 50. Since only one primer is capable of supporting elongation, there can be no amplification of the region 40 following subsequent cycles of synthesis and annealing of primers.

Shown in FIG. 3 is a reference DNA molecule 42 which has been previously characterized and shown not to include target sequence 10, 12. Annealed to the first strand 46 of the reference molecule 42 is a third primer 52. Third primer 52 includes a template binding region 54 which corresponds essentially to the template binding region 16 of the first primer 14. Template binding region 54 is complementary to and hybridizes with the primer binding position 56 of the first strand 46 and corresponds generally to the primer binding position 18 of the first strand 4 of the selected DNA molecule 2. Third primer 52 does not include a target sequence binding region 20 and, instead, includes a wild type sequence complementary region 58 that comprises at least one nucleotide that is complementary to the corresponding nucleotide 60 on the first strand 46 of the reference DNA molecule 42. The nucleotide or nucleotides of the wild type sequence region 60 will be in a position corresponding to the target sequence 10, 12 when target sequence 10, 12 is absent from the identified region 8 or 44.

Also shown in FIG. 3 is a fourth primer 62 having a template binding region 64 which recognizes a primer binding position 66 on the second strand 48 of the reference DNA molecule 42. The template binding region 64 and primer binding position 66 may correspond, respectively, to template binding regions 26 and primer binding position 28 shown in FIG. 1A. However, these sites may be distinct from those selected for the construction of primer molecule 24.

When the DNA molecule 42 and associated third and fourth primers 52, 62 are subjected to chain elongation, newly synthesized chains 68 and 70 are generated. Thus, primers 52 and 62 are able to successfully amplify the desired DNA.

However, as shown in FIG. 3B, when the third and fourth primers 52, 62 are applied to the selected DNA molecule 2 which includes target sequence 10, 12 within identified region 8, amplification is not achievable. This is due to the fact that although the third primer is capable of hybridizing with the first strand 4 by means of template binding region 54 and primer bin 18, a 3' terminal flap results from the inability of the hybridize with the target sequence 10. Of course, the fourth primer 62 is capable of hybridizing with the second strand 6 by means of primer binding region 64 and is capable of priming chain elongation 70. However this chain extension will not result in amplification of the desired region.

Turning now to FIGS. 4A through 4D are shown the foregoing concepts in the context of a point mutation, of the insertion variety, i.e., where the particular target sequence is a insertion point mutation of the DNA. Shown in FIG. 4A is a selected DNA molecule 72 having a first strand 74 and a second strand 76. Contained within the selected DNA molecule 72 is an identified region 78, such as a gene, which includes a point mutation 80, 82 on its first and second 74, 76, respectively.

In the hypothetical depiction in FIG. 4A, the point mutation is intended to denote the inclusion of an additional A/T nucleotide pair into the identified region 78. Thus, when the point mutation is present, the nucleotide sequence along the first strand 74 is -T-A-C-A-, whereas when the point mutation is not present, as depicted in FIG. 4B, the nucleotide sequence along the first strand 84 will be -T-C-A-, thus missing the second "A" residue. In FIG. 4A is also shown a first primer 86 having a template binding region 88 that is capable of hybridizing with the corresponding primer binding position 90 on the first strand 74. The first primer 86 further includes at its 3' terminus a target sequence complementary region 92 that consists of a 3' terminal T residue. As depicted therein, in that primer 86 includes a 3' terminus capable of forming a hybrid with the target sequence, the primer is able to prime chain elongation 94. course, second primer 96 is similarly capable of priming chain elongation in an opposite direction along second strand 76.

However, when the same two primers 86, 96 are employed in an attempt to prime synthesize from a reference wild type DNA 98 which includes an identified region 84 that does not exhibit the point mutation 80, 82, amplification is not achieved. This is because the target sequence complementary region 92 of first primer 86 will not form a hybrid with the wild type nucleotide 100 which occupies the position which would have been the target sequence if the target sequence were present.

Shown in FIG. 4C is a representation of the benefits achieved when a nonsense nucleotide in included in the first primer construct. Shown in FIG. 4C is the same DNA molecule and identified region as that shown in FIG. 4A. However, the first primer 86 has been modified by the inclusion of a nonsense nucleotide 102 which is not complementary to the corresponding nucleotide 104. As noted, it has been found that the complementarity between target sequence complementary nucleotide 92 and target sequence 80 is adequate to achieve priming and chain elongation 106.

When the same first primer 108 which includes nonsense nucleotide 102 is applied to wild type DNA molecule 98, as shown in FIG. 4D, the priming is not achieved. This is because neither the target sequence complementary region 92 nor nonsense nucleotide 102 are capable of forming a hybrid with the template strand.

The following examples are included to exemplify the practice of the invention. The examples represent laboratory studies conducted or contemplated by the inventors and are disclosed in terms of standard laboratory practices found by the inventors to work well in the context of the embodiments in which they refer. However, those of skill in the art will appreciate that these examples are meant to be representative only, and numerous modifications in the examples will be apparent to those of skill in light of the present disclosure.

EXAMPLE I

The Detection of Point Mutations in the L-RAS Gene

This example demonstrates how the present invention is applied for design of primers to distinguish normal alleles of the K-RAS proto-oncogene from alleles containing point mutations at codon 12 in colon carcinoma.

Primers

The following twenty oligomer synthetic nucleotide primer is complementary to the normal sequences of the K-RAS proto-oncogene: 5'-CTTGTGGTAGTT-GGAGCTGG-3'. The primer directed at a mutation of the K-RAS oncogene found in colon carcinoma, and in particular, SW480 and SW403 colon carcinoma cell lines, contains a guanine to thymine switch in the middle position of the 12th codon.

A primer was constructed as follows to incorporate the thymine mutation in the 3' terminus: 5'-CTTGTGGTAGTTGGAGCTGT-3' The remainder of the primer is composed of normal complementary sequences to the K-RAS gene. In both instances the same twenty oligonucleotide synthetic primer was used for amplification of the opposite strand and was located at a distance 56 nucleotides 3' from the above primers. The primer represents complementary sequences of 20 nucleotides in length to the opposite strand of the K-RAS gene: 5'-CTCTATTGTTGGATCATATT-3'.

DNA specimen extraction

Human DNA specimens from SW480 and SW403 colon carcinoma cell lines and HL60 leukemia cell line were extracted by standard technique of proteinase K digestion and phenol/chloroform extraction (Ausubel, et al. Eds.: Current Protocols in Molecular Biology. Chapter 2, section 1 and 2. Greene Publishing Assoc. and Wiley-Interscience, New York, 1987).

Amplification

Since the genomic DNA is double stranded it is necessary to separate the two strands by heat denaturation at 95° C. for five minutes in a heat block. Two Eppindorf tubes were prepared for each cell line. The first tube contained one microliter of DNA in 10 microliters of a 10x reaction buffer which consisted of 100 mM Tris-HCL pH 8.3 (at 25° C.), 500 mM KCL, 15 mM MgCl2, 0.1% (w/v) gelatin (Sigma, St. Louis, Mo.); 200 micromolar of deoxynucleotides (dATP, dCTP, dGTP, and dTTP); 1.0 micromolar of each primer in the normal K-RAS primer set; 2.5 units of Taq DNA polymerase; and double distilled sterile water to reach a total volume of 100 microliters. The second tube contained in the same components as above except that the normal K-RAS primer set was replaced with the K-RAS codon 12 mutation primer and the normal primer to the opposite strand. The concentration of the primers added was 1.0 micromolar each. The tubes were overlayed with two drops of mineral oil and placed in a heat block and amplified as follows: denaturation at 95° C. for 1.5 minutes, annealing at 50° C. for 2 minutes, and extension at 72° C. for 1 minute for 30 cycles.

Ten microliter aliquots from each tube were removed and loaded onto a 4% Nusieve agarose gel with lane one of the gel containing the marker phi X174 as a control for size fragmentation. The gel was electrophoresed for 45 minutes at 75 Volts then stained with ethidium bromide for 15 minutes followed by a ten minute rinse in distilled water. Under ultraviolet fluorescent examination the gel revealed a band of the expected size, 96 nucleotides, as determined in reference to the marker phi X174 in the lanes which corresponded to the normal K-RAS primer set for HL60 and SW403 cell lines. SW480 contains only mutated K-RAS alleles therefore no band corresponding to the normal allele was present. Aliquots from the amplifications which contained the mutated K-RAS primer had the following results. In the lane with HL60, which does not contain a mutated K-RAS codon 12, no band of 96 nucleotides was seen. In the lanes corresponding to SW480 and SW403 a band of 96 nucleotides was present.

To further confirm the findings the agarose gels were transferred by the Southern technique onto a Nylon filter and hybridized by standard technique of sequence specific probe hybridization as described (Verlaan-de-Vries, et al.: A dot blot screening procedure for mutated ras oncogenes using synthetic oligonucleotides. Gene, 50:313-320, 1986). The probes corresponded to the 3' terminus of the primer with or without the known mutation: normal probe 5'-GCTGGTGGCGTAGG-CAAGAG-3' and the mutated probe 5'-GCTGTTGGCGTAGGCAAGAG-3' The probes could not confirm the presence of the normal 12th codon or the mutated codon since the amplified strand would contain the sequence of the respective primer used. However, the probe would confirm the elongation of a strand corresponding to the K-RAS gene. For HL60 hybridization with the normal K-RAS probe revealed a band with the normal primer set only and no band with the mutated primer as was expected. SW403 hybridized with the normal probe revealed a band in the aliquot with the normal primer set but not the mutated primer set and SW480 revealed no band in either primer set. When hybridized with the mutated probe only the SW403 and SW480 aliquots from the mutated primer set demonstrated a band.

EXAMPLE II

The Detection of Point Mutations in the N-RAS Gene

This example demonstrates how the present invention is applied for design of primers to distinguish normal alleles of the N-RAS proto-oncogene from alleles containing point mutations at N-RAS codon 61 in leukemia.

Primers

The following twenty oligomer synthetic nucleotide primer is complementary to the normal sequences of the N-RAS proto-oncogene: 5'-ATACT-GGATACAGCTGGACG-3'. The primer directed at a mutation of the N-RAS oncogene found in acute leukemia and in particular, HL60 leukemia cell line, contains a guanine to thymine switch in he 61st codon. A primer was constructed as follows to incorporate the thymine mutation in the 3' terminus: 5'-ATACT-GGATACAGCTGGACT-3'. The remainder of the primer is composed of normal complementary sequences to the N-RAS gene. In both instances the same twenty oligonucleotide synthetic primer was used for amplification of the opposite strand and was located at a distance 49 nucleotides 3' from the above primers. The primer represents complementary sequences of 20 nucleotides in length to the opposite strand of the N-RAS gene: 5'-GTTGGATCATATTCGTCCAC-3'.

DNA specimen extraction

Human DNA specimens from SW480 colon carcinoma cell line and HL60 leukemia cell line were extracted by standard technique of proteinase K digestion and phenol/chloroform extraction (Ausubel, et al. Eds.: Current Protocols in Molecular Biology. Chapter 2, section 1 and 2. Greene Publishing Assoc. and Wiley-Interscience, New York, 1987).

Amplification

Since genomic DNA is double stranded the two strands were separated by heat denaturation at 95° C. for five minutes in a heat block. Two eppindorf tubes were prepared for each cell line. The first tube contained one microliter of DNA in 10 microliters of a 10x reaction buffer which consisted of 100 mM Tris-HCL pH 8.3 (at 25° C.), 500 mM KCL, 15 mM MgCl2, 0.1% (w/v) gelatin (Sigma, St. Louis, Mo.); 200 micromolar of deoxynucleotides (dATP, dCTP, dGTP, and dTTP); 1.0 micromolar of each primer in the normal N-RAS codon 61 primer set; 2.5 units of Taq DNA polymerase; and double distilled sterile water to reach a total volume of 100 microliters. The second tube contained in the same components as above except that the normal N-RAS primer set was replaced with the N-RAS codon 61 mutation primer and the normal primer to the opposite strand. The concentration of the primers added was 1.0 micromolar each. The tubes were overlayed with two drops of mineral oil and placed in a heat block and amplified as follows: denaturation at 95° C. for 1.5 minutes, annealing at 50° C. for 2 minutes, and extension at 72° C. for 1 minute for 30 cycles.

Ten microliter aliquots from each tube were removed and loaded onto a 4% Nusieve agarose gel with lane one of the gel containing the marker phi X174 as a control for size fragmentation. The gel was electrophoresed for 45 minutes at 75 Volts then stained with ethidium bromide for 15 minutes followed by a ten minutes rinse in distilled water. Under ultraviolet fluorescent examination the gel revealed a band of the expected size, 89 nucleotides, as determined in reference to the marker phi X174. The expected size bands were present in the lanes which corresponded to the normal N-RAS primer set for HL60 and SW403 cell lines and in the lane with the mutated primer set and HL60. SW480 did not display a band with the mutated primer set as expected since the cell line does not contain a mutated N-RAS codon 61.

To further confirm the findings the agarose gels were transferred by the Southern technique onto a nylon filter and hybridized by standard technique of sequence specific probe hybridization as described (Verlaan-de-Vries, et al.: A dot blot screening procedure for mutated ras oncogene using synthetic oligonucleotides. Gene, 50:313—320, 1986). The probes corresponded to the 3' terminus of the primer with or without the known mutation: normal N-RAS codon 62 probe 5'-GGACAAGAAGAGTACAGTGC-3' and the mutated probe 5'-GGACTAGAAGAGTACAGTGC-3'. The probes could not confirm the presence of the normal 61st codon or the mutated codon since the amplified strand would contain the sequence of the respective primer used. However, the probe would confirm the elongation of a strand corresponding to the N-RAS gene. For HL60 hybridization with the normal K-RAS probe revealed a band with the normal primer set only and a band was seen with the mutant probe and the mutated primer was expected since the cell line has one mutated and one normal allele. SW480 hybridized with the normal probe with the aliquot from the normal primer set, but not with the mutated primer set and hybridization with the mutant probe revealed no bands on either primer set.

The foregoing description of the present invention has been made in term of preferred embodiments found by the present inventors to function well in the practice of the invention. However, those of skill in the art will appreciate that various modifications and changes may be made in he foregoing embodiments, in light of the present disclosure, and nevertheless achieve a like result. All such modifications and changes as may be apparent to those of skill are intended to be within the spirit and scope of the invention and the appended claims.

What is claimed is:

1. A method for detecting the presence or absence of a target DNA sequence within an identified region of a selected DNA molecule, wherein when the target is present in the region, it has an expected location and configuration therein, the method comprising the steps of:
   (a) obtaining a nucleic acid primer molecule having a template binding region that is capable of hybridizing to a first strand of the selected DNA molecule at a binding position 3' of and adjacent to the expected location of such a target sequence within the DNA molecule, said template binding region of the primer molecule being capable of binding to said DNA molecule when the target sequence is present or absent, the primer molecule further including at its 3' terminus and adjacent the template binding region a target sequence complementary region comprised of at least one nucleotide complementary to a corresponding nucleotide of the target sequence, said primer being capable of priming polymerase chain extension when said target sequence is present on said DNA molecule, yet incapable of priming polymerase chain extension when the target sequence is absent; and
   (b) determining the ability of the primer molecule to prime the polymerase chain extension using the selected DNA molecule as a template, to detect the presence or absence of the target sequence within the selected DNA molecule.

2. The method of claim 1, wherein determining the ability of the primer molecule to prime polymerase chain extension includes the steps of:
   (a) obtaining a second nucleic acid primer molecule having a second template binding region that is capable of hybridizing to the second strand of the selected DNA molecule at a binding position 3' of the expected location of such a target sequence; and
   (b) determining the ability of the first and second primers to prime polymerase chain reaction synthesis of both strands of the DNA molecule, such an ability being indicative of the presence of the target sequence within the selected DNA molecule.

3. The method of claim 2, wherein determining the ability of the first and second primers to prime polymerase chain reaction synthesis includes the steps of:
   (a) hybridizing the primers with the selected DNA molecule to form primed templates;
   (b) subjecting the primed templates to polymerase chain extension to form polymerase chain extended products; and
   (c) detecting the generation of polymerase chain extended products having a size corresponding to about the cumulative size of the first and second primers and the distance between their respective primer binding positions along the DNA molecule.

4. The method of claim 3 wherein detecting the generation of polymerase chain extended products comprises subjecting the polymerase chain extended products to gel electrophoresis, and identifying products of the appropriate size.

5. The method of claim 4 wherein generated polymerase chain extended products are identified by means of a label.

6. The method of claim 2, further including determining the ability of the primer molecules to prime polymerase chain extension using a reference DNA molecule 42 as template, the reference molecule having such an identified region 44 which has been characterized in terms of the presence or absence of the target sequence.

7. The method of claim 1, wherein the primer molecule further includes, at a position 1 to 3 nucleotides 5' of the target sequence complementary region and positioned between the template binding region and the target sequence complementary region, a nonsense nucleotide that is not complementary to its corresponding nucleotide on the selected DNA molecule.

8. The method of claim 6, wherein the identified region of the selected and reference DNA molecule comprises a selected gene and the target DNA sequence comprises a mutation in said gene.

9. The method of claim 8, wherein the mutation comprises a sequence present in the selected DNA molecule and absent from the reference DNA molecule.

10. The method of claim 8, wherein the mutation comprises a sequence absent from the selected DNA molecule and present in the reference DNA molecule.

11. The method of claim 9 or 10, wherein the target sequence comprises a point mutation, and the target sequence complementary region of said primer comprises a nucleotide that is complementary to the point mutation.

12. The method of claim 9 or 10, wherein the target sequence comprises an insertion mutation, and the target sequence complementary region comprises at least one nucleotide that is complementary to the 3' nucleotide of the insertion.

13. The method of claim 9 further comprising the steps of:
   (a) obtaining a third nucleic acid primer molecule having a third template binding region that is capable of hybridizing to a first or second strand of the selected DNA molecule at a binding position 3' of and adjacent to the expected location of such a target sequence within the DNA molecule, said template binding region of the primer molecule being capable of binding to said DNA molecule when the target sequence is either present or absent, the primer molecule further including at its 3' terminus and adjacent the template binding region at least one nucleotide complementary to the corresponding nucleotide on the reference DNA molecule, said primer being capable of priming polymerase chain extension when said target is present on the DNA molecule, yet incapable priming polymerase chain extension when the target sequence is absent; and
   (b) determining the ability of the third primer molecule to prime the polymerase chain extension using the selected DNA molecule as a template, to detect the presence or absence of the target sequence within the selected DNA molecule.

14. The method of claim 13, wherein the third template binding region corresponds to the first template binding region.

15. The method of claim 13, wherein determining the ability of the third primer molecule to prime polymerase chain extension includes the steps of:
   (a) obtaining a fourth nucleic acid primer molecule having a fourth template binding region that is capable of hybridizing to the opposite strand from the third primer molecule at a binding position 3' of the expected location of such a target sequence; and
   (b) determining the ability of the third and fourth primers to prime polymerase chain extension on both strands of the reference or selected DNA molecule, such an ability being indicative of the absence of the target sequence within the respective DNA molecule.

16. The method of claim 15, wherein the fourth nucleic acid primer molecule corresponds to the second nucleic acid primer molecule.

17. A method for detecting the presence or absence of a point mutation within a selected gene of a selected DNA molecule, wherein when said point mutation is present in the gene, it has an expected location and configuration therein, the method comprising the steps of:
   (a) obtaining a nucleic acid primer molecule having a template binding region that is capable of hybridizing to a first strand of the selected DNA molecule at a binding position 3' of and adjacent to the expected location of the point mutation, said template binding region of the primer molecule being capable of binding to said DNA molecule when the point mutation is either present or absent, the primer molecule further including at its 3' terminus and adjacent the template binding region a nucleotide that is complementary to the point mutation, said primer being capable of priming polymerase chain extension when said point mutation is present on said DNA molecule, yet incapable of priming polymerase chain extension when the point mutation is absent; and
   (b) determining the ability of the primer molecule to prime polymerase chain extension using the selected DNA molecule as a template, to detect the presence or absence of the point mutation within the selected DNA molecule.

18. The method of claim 17, wherein determining the ability of the primer molecule to prime polymerase chain extension includes the steps of:
   (a) obtaining a second nucleic acid primer molecule having a second template binding region that is capable of hybridizing to the second strand of the selected DNA molecule at a binding position 3' of the expected location of such a point mutation; and
   (b) determining the ability of the first and second primes to prime polymerase chain reaction synthesis of both strands of the DNA molecule, such an ability being indicative of the presence of the point mutation in the expected configuration within the selected DNA molecule.

19. The method of claim 18, further including determining the ability of the first and second primer molecules to prime polymerase chain extension using a reference DNA molecule as template, the reference molecule known to include the gene without the point mutation.

20. A nucleic acid primer molecule for use in connection with polymerase chain extension for detecting the presence or absence of a target DNA sequence that has an expected location and configuration within an identified region of a selected DNA molecule, the nucleic acid primer molecule having a template binding region that is capable of hybridizing to a first strand of the selected DNA molecule at a binding position 3' of and adjacent to the expected location of such a target sequence within the DNA molecule, the primer molecule further including at its 3' terminus and adjacent the template binding region at target sequence complementary region comprised of at least one nucleotide complementary to a corresponding nucleotide of the target sequence.

21. The primer molecule of claim 20, further including, at a position 1 to 3 nucleotides 5' of the target sequence complementary region and positioned between the template binding region and the target sequence complementary region, a nonsense nucleotide that is not complementary to its corresponding nucleotide on the selected DNA molecule.

22. The primer molecule of claim 20, wherein the target sequence comprises a point mutation, and the target sequence complementary region of said primer comprises a nucleotide that is complementary to the point mutation.

* * * * *

UNITED STATES PATENT AND TRADEMARK OFFICE
CERTIFICATE OF CORRECTION

PATENT NO. : 5,137,806
DATED : August 11, 1992
INVENTOR(S) : LeMaistre, et al

It is certified that error appears in the above-indentified patent and that said Letters Patent is hereby corrected as shown below:

In Claim 6, column 26, line 12, delete --42--.

In Claim 6, column 26, line 13, delete --44--.

In Claim 18, column 28, line 10, delete --primes-- and insert therefor "primers".

Signed and Sealed this

Fourteenth Day of September, 1993

Attest:

BRUCE LEHMAN

Attesting Officer          Commissioner of Patents and Trademarks